United States Patent [19]

Taugner et al.

[11] 4,024,779
[45] May 24, 1977

[54] ANTI-ROLL DEVICE FOR ULTRAMICROTOMES

[75] Inventors: Roland Taugner; Juergen Eschwey, both of Heidelberg, Germany

[73] Assignee: C. Reichert Optische Werke, Vienna, Austria

[22] Filed: Jan. 28, 1976

[21] Appl. No.: 652,952

[30] Foreign Application Priority Data

Feb. 14, 1975 Germany .......................... 2506255

[52] U.S. Cl. .................................. 83/165; 83/915.5
[51] Int. Cl.² ...................... B26D 7/06; G01N 1/06
[58] Field of Search ................... 83/915.5, 165, 162

[56] References Cited
UNITED STATES PATENTS

| | | | |
|---|---|---|---|
| 3,225,639 | 12/1965 | Martinelli | 83/915.5 X |
| 3,227,020 | 1/1966 | Zeytoonian | 83/915.5 X |
| 3,733,948 | 5/1973 | Pickett | 83/915.5 X |

*Primary Examiner*—Willie G. Abercrombie
*Attorney, Agent, or Firm*—Alan H. Spencer; William C. Nealon; Howard R. Berkenstock, Jr.

[57] ABSTRACT

Ultramicrotomes conventionally use a glass fragment, or fragment of similar material, as a knife. Such knives have the disadvantage of an uneven back surface inherent in the production of such a knife by fragmentation. Using the complementary fragment and mounting the same slightly spaced from the knife back, provides an anti-curl device. A knife holder, having a groove in which the knife fragment is mounted and a pivoted member with a matching slot to hold the anti-curl device, provides positioning of the anti-curl device and provides access to the specimen when the anti-curl device is pivoted out of proximity of the cutting edge.

8 Claims, 5 Drawing Figures

ANTI-ROLL DEVICE FOR ULTRAMICROTOMES

BACKGROUND OF THE INVENTION

This invention relates to ultramicrotome knives and in particular, to anti-curl devices for ultramicrotome knives produced by fragmenting a glass-like substance and holders therefor.

Ultramicrotomes are used to produce specimen slices which are extremely thin in comparison with the usual microtomes. For example, a conventional microtome will produce specimen slices having thicknesses in the order of one micron. Ultramicrotomes, however, are used to produce slices as thin as 50A. These slices are so thin that it is frequently impossible to see the same without optical assistance and are so fragile as to cause extreme difficulty in removal and handling.

Because of the fragility of the ultra-thin slices produced by ultramicrotomes, the specimen slices have conventionally been collected by floating the same on fluids. Usually, the ultramicrotome knife is surrounded or partly surrounded by a small trough in which a fluid having a density greater than the specimen is contained. As specimens are cut, they float on the liquid and may be collected therefrom. This procedure has two disadvantages. The first is that there is an ever-increasing demand for cryogenic temperatures during sectioning. While fluids, such as dimethyl sulfoxide, may be used to temperatures of about −50° C., at lower temperatures, fluids are not available for floating section slices. It has also been recently determined that some form of ion exchange action takes place between the tissue section and the support fluid. This ion exchange action has deleterious effects on the tissue specimen and complicates both examination and analysis.

Steel microtome knives, which are used to cut specimen thicknesses of one micron or more, have a regular back surface. The regularity of the back surface makes it relatively easy to provide an anti-curl device. Such devices are disclosed in U.S. Pat. Nos. 3,599,523; 3,699,830 and 3,733,948. If the knife is a conventional knife, rather than disposable, the anti-curl device is conventionally a flat plate piece of glass or plastic which is adjustable to be positioned in a parallel-spaced relationship to the knife back. In operation, the specimen section proceeds from the knife edge as it is cut to the space between the anti-curl device and the knife back.

It is an object of the present invention to provide an anti-curl device for irregular shaped microtome knife backs;

It is another object of the present invention to provide an anti-curl device for glass ultramicrotome knives; and It is still another object of the present invention to provide a holder for ultramicrotome knives and anti-curl devices.

BRIEF DESCRIPTION OF THE PRESENT INVENTION AND DRAWINGS

The anti-curl device of the present invention is prepared by salvaging the complementary fragment formed during the preparation of a glass or similar ultramicrotome knife. Since this section is in fact complementary to the back of an ultramicrotome knife, it has a surface uniformly matching the surface of the knife. Thus, if the complementary fragment is properly positioned, there will be a uniform space between the complementary surfaces providing the necessary gap to accommodate ultra-thin sections as they are sliced by the knife.

A further advantage, of using the complementary fragment formed when the knife is made, lies in its transparency. The transparency permits observation of a specimen section, even if it is ultra-thin.

Glass microtome knives are usually fabricated by a microtomist when he needs the same, rather than be a commercial manufacturer. Thus, it would be extremely difficult for a manufacturer to preform ultramicrotome anti-curl devices, since the configuration of the glass knife back is not known until it actually is fabricated. One particular advantage of the present invention is that the microtomist prepares the anti-curl device at the same time he fabricates the knife. The holder of the present invention then enables the microtomist to mount both the knife and the anit-curl device in the proper relationship for use.

DETAILED DESCRIPTION OF THE PRESENT INVENTION

Figure 1:
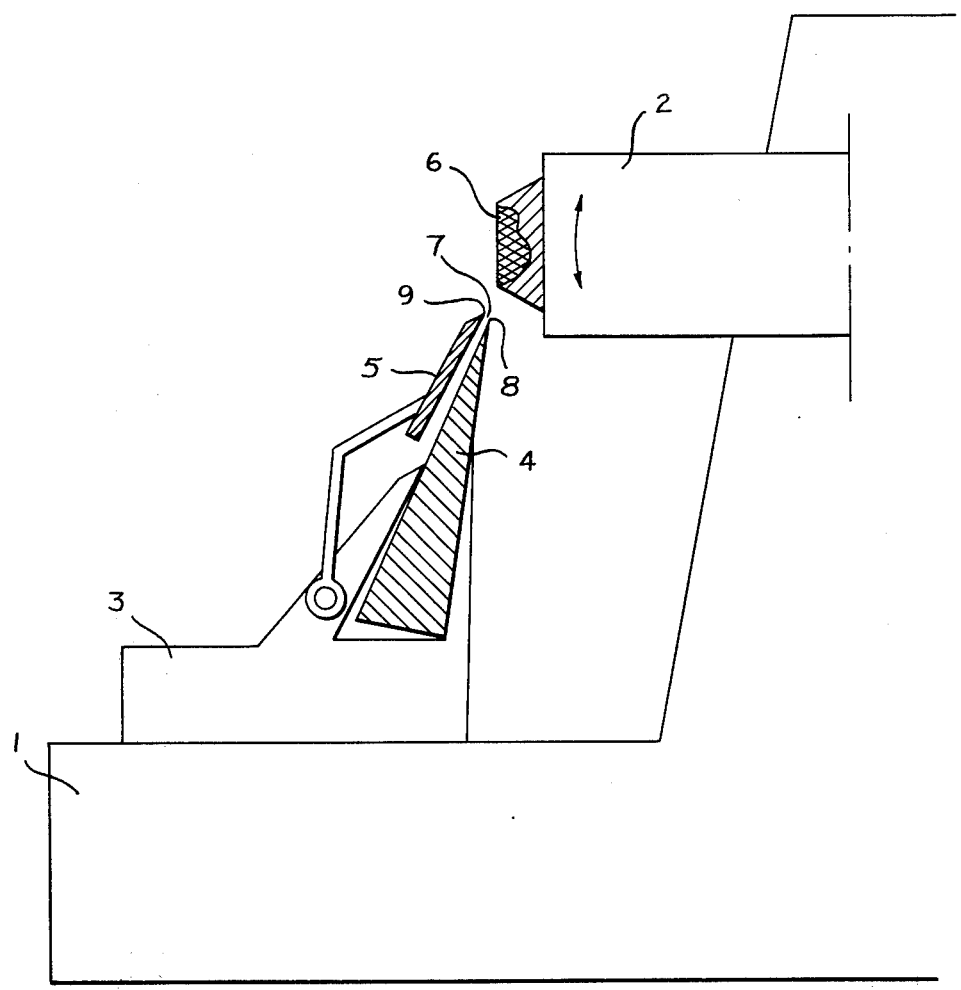
FIG. 1 is a schematic representation of a knife, anti-curl device and specimen in operational relationship in an ultramicrotome.

Referring to FIG. 1, ultramicrotome 1 has specimen arm 2 which oscillates in a vertical direction as specimens are cut. Knife holder 3 is positionable on the ultramicrotome to locate knife 4 in the proper relationship with specimen 6 to be cut. Anti-curl device 5 is pivotably mounted to knife holder 3 in order that the specimen may be removed from gap 7. Knife 4 is shown as a metal knife for convenience and as the surface of specimen 6 engages the edge 8 of knife 4, the specimen is prevented from curling after cutting by leading edge 9 of anti-curl device 5.

Figure 2A:
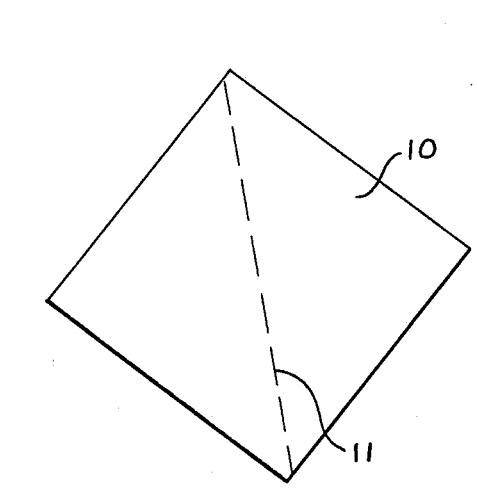
FIG. 2a illustrates a piece of glass scored in preparation for preparing an ultramicrotome knife.

FIG. 2a represents a glass block 10 having a score line 11 along which block 10 is to be broken. For convenience, the glass block may be rectangular and preferably square with a linear surface dimension in the order of 2.5 cm.

Figure 2B:
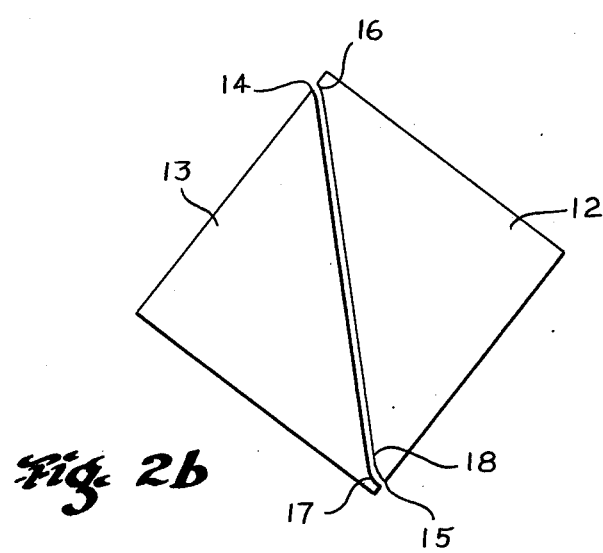
FIG. 2b shows a side view of the ultramicrotome knife and anti-curl device after breaking the glass along the score line.

FIG. 2b illustrates the component parts 12 and 13 resulting from breaking block 10. Part 13 has cutting edge 14 and component 12 has cutting edge 15. Complementary surfaces 16 and 17 match to provide a substantially uniform gap 18 therebetween, behind cutting edges 14 and 15.

Figure 3:
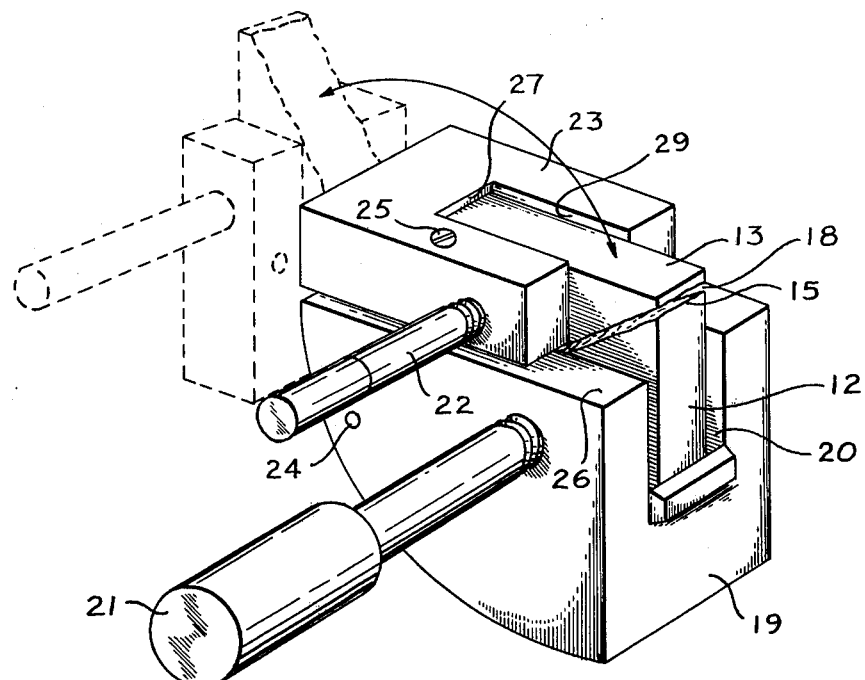
FIG. 3 shows a knife holder having a glass ultramicrotome knife and anti-curl device mounted therein.
Figure 4:
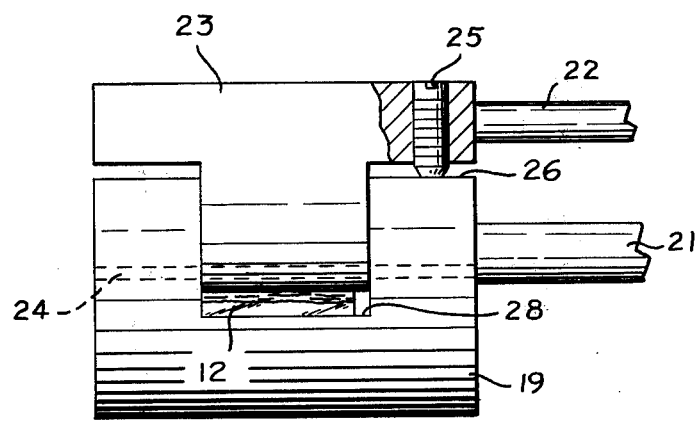
FIG. 4 shows the back of the ultramicrotome knife holder of FIG. 3.

In FIG. 3, knife holder body 19 is adjustably mounted to a base (not shown) in a manner to provide versatility in positioning on the ultramicrotome. Body 19 has an elongated recess 20 in the top extending the entire distance front to back. Component part 12 is held in recess 20 by clamp screw 21 and presents cutting edge 15 for sectioning. Component part 13 is held by clamp screw 22 in groove 29 of carrier 23. Carrier 23 is pivotably mounted by pin 24 to body 19 in order that carrier 23 may be swung to the dotted position shown, to provide access for removal of tissue sections after cutting. Gap 18 between complementary surfaces 16 and 17 of component parts 12 and 13, respectively, is adjusted by means of screw 25 which bears against surface 26. The back 27 of the groove 29 and bottom 28 of body recess 20 are preferably arranged at a precise angle of 90° to each other when carrier 23 is flush on surface 26 of body 19, in order that the complementary parts 12 and 13 can be easily aligned by virtue of preferred rectangular surfaces and gap 18 is then obtained by slightly raising carrier 23 from surface 26 using screw 25.

It is of great convenience to have recess 20 and groove 29 arranged with one wall of each in a common plane. Usually, the walls being in the common plane are the ones opposite clamp screws 21 and 22. This arrangement substantially eliminates lateral alignment problems if glass block 10 is broken in a plane perpendicular to one side as shown in FIGS. 2a and 2b.

Obviously, a slide arrangement permitting vertical and/or horizontal positioning of carrier 23 relative to body 19 can be used instead of the pivot arrangement shown. Such an arrangement could utilize the conventional dovetail and groove slide with a manually operable micrometer screw for adjustment.

What is claimed is:

1. In an ultramicrotome for cutting specimen sections, the improvement comprising two glass fragments of a single piece of glass, said fragments having complementary surfaces, and being mounted with said complementary surfaces spaced juxtaposition and one of said fragments having a sharp leading edge for cutting specimen sections whereby the cutting enters the space between said complementary surfaces as the specimen is cut to prevent curling thereof.

2. The improvement of claim 1 wherein said fragments comprise substantially the entire piece of glass.

3. The improvement of claim 1 wherein each of said fragments has a pair of parallel planar sides normal to said complementary surfaces.

4. A microtome glass knife and complementary glass anti-curl device holder comprising a body, a groove extending across one surface of said body, said groove having a planar side, first retaining means for holding a glass knife in said groove and against said side, a carrier mounted on said body, said carrier having a recess extending across one entire surface thereof, said recess having a planar side wall, said wall being coplanar with said side and second retaining means for holding a complementary glass anti-curl device against said wall and juxtapositioned to the knife.

5. The holder according to claim 4 wherein a pivot mounts said carrier on said body.

6. The holder according to claim 5 wherein said pivot has an axis normal to said side.

7. The holder according to claim 4 wherein said groove and said recess have a rectangular cross section.

8. The holder according to claim 4 wherein said first and second retaining means manually operable threaded members.

* * * * *